United States Patent [19]
Ramachandran et al.

[11] Patent Number: 5,900,393
[45] Date of Patent: May 4, 1999

[54] SCALP CARE PRODUCTS CONTAINING ANTI ITCHING /ANTI IRRITANT AGENTS

[75] Inventors: Pallassana Narayanier Ramachandran, Robbinsville; Clarence Ralph Robbins, Martinsville; Amrit Manilal Patel, Dayton, all of N.J.

[73] Assignee: Colgate-Palmolive Company, New York, N.Y.

[21] Appl. No.: 08/668,803

[22] Filed: Jun. 24, 1996

Related U.S. Application Data

[63] Continuation of application No. 08/411,884, Mar. 31, 1995, abandoned.

[51] Int. Cl.$^6$ .............................. C11D 1/02; C11D 1/94; C11D 3/28
[52] U.S. Cl. .............. 510/124; 510/122; 510/125; 510/127; 510/131; 510/137; 510/138; 510/159; 510/386; 510/500; 510/501; 510/504; 424/70.19; 424/70.21; 424/70.24; 424/70.27; 514/852; 514/385; 514/396
[58] Field of Search ................... 510/122, 124, 510/125, 127, 131, 137, 138, 159, 386, 500, 501, 504; 424/70.19, 70.21, 70.24, 70.27; 514/852, 385, 396

[56] References Cited

U.S. PATENT DOCUMENTS

| | | | |
|---|---|---|---|
| 3,812,142 | 5/1974 | Meiser et al. | 260/309 |
| 3,903,287 | 9/1975 | Meiser et al. | 424/273 |
| 4,329,334 | 5/1982 | Su et al. | 424/70 |
| 4,329,335 | 5/1982 | Su et al. | 424/70 |
| 4,329,336 | 5/1982 | Su et al. | 424/70 |
| 4,835,148 | 5/1989 | Barford et al. | 514/179 |
| 4,867,971 | 9/1989 | Ryan et al. | 424/81 |
| 5,106,613 | 4/1992 | Hartnett et al. | 424/71 |
| 5,151,209 | 9/1992 | McCall et al. | 252/174.15 |
| 5,384,114 | 1/1995 | Dowell et al. | 424/70.1 |

FOREIGN PATENT DOCUMENTS

| | | |
|---|---|---|
| 136914 | 4/1985 | European Pat. Off. . |
| 312234 | 4/1989 | European Pat. Off. . |

*Primary Examiner*—Douglas J. McGinty
*Assistant Examiner*—Gregory R. Delcotto
*Attorney, Agent, or Firm*—Richard J. Ancel; Rosemary M. Miano; Richard N. Miller

[57] ABSTRACT

Mild aqueous detergent, e.g., shampoo, compositions are disclosed based on a mixture comprising anionic surfactant and amphoteric surfactant, such as betaines, present in the composition at a level of from about 0.75 to 1.25 parts by weight per part by weight of anionic surfactant. The compositions also contain one or a mixture of therapeutic agents such as climbazole or a mixture of climbazole and one or more co-therapeutics such as salicylic acid. The combination of mild surfactant system and therapeutic agent serve to prevent or treat mild skin disorders such as scalp itch and scalp irritation when applied to the scalp as a shampoo. Shampoo compositions also preferably contain one or more conditioning agents and suitable suspending agents.

18 Claims, No Drawings

5,900,393

SCALP CARE PRODUCTS CONTAINING ANTI ITCHING /ANTI IRRITANT AGENTS this is a continuation of pending prior application Ser. No. 08/411,884 filed Mar. 31, 1995, now abandoned.

BACKGROUND OF THE INVENTION

1. Field of the Invention

The invention relates to skin care compositions which exhibit a therapeutic effect in the treatment of skin disorders such as itching, irritation and skin dryness.

2. Description of Related Art

There are a number of shampoo products on the market today which are specifically formulated as anti-dandruff shampoos. These products generally contain one or a mixture of surfactants, with the primary surfactant being an anionic surfactant such as an alkyl or aryl sulfate or sulfonate. One hypothesis is that dandruff problems are believed to be linked to the presence of a yeast-like fungus on the skin and an acceleration of the normal process of skin production. Conventional anti-dandruff shampoos generally contain effective amounts of an active agent which inhibits fungal growth and/or slows cell growth on the scalp. Examples of these agents include zinc pyrithione, selenium sulfide, salicylic acid, coal tar, sulfur, ketoconozole and climbazole. Examples of typical anti-dandruff shampoo formulations are disclosed in U.S. Pat. Nos. 4,089,945; 4,329, 334; 4,329,335; 4,329,336 and 4,835,148.

However, experience has shown that excessive dandruff is largely a problem associated with cold, dry climates and it generally does not occur until after puberty. In more humid, tropical regions dandruff is a much less common disorder. However, inhabitants of these regions are generally more susceptible to mild forms of scalp dermatitis with such symptoms as excessive scalp itching, scalp irritation, inflammation, scalp dryness and scalp redness. These symptoms can also occur during the warm summer months in non-tropical regions. Although many of these symptoms ought to be relieved by the use of the anti-fungal agents present in some anti-dandruff shampoos, e.g., climbazole, zinc pyrithione or selenium sulfide, experience has demonstrated that these symptoms are not relieved and, in fact, are even worsened by regular use of many commercial anti-dandruff hair shampoos.

Accordingly it is a primary object of this invention to provide a mild, aqueous, skin care detergent composition, e.g., a scalp care shampoo or a shower cleansing composition, which exhibits a therapeutic effect on skin disorders, particularly, scalp disorders, particularly as encountered in warm weather and in tropical regions.

SUMMARY OF THE INVENTION

The present invention provides a mild aqueous, detergent composition, e.g., a shampoo composition, having a therapeutic effect on skin and scalp disorders comprising an aqueous dispersion of: (a) from about 5 to about 12% by weight of anionic surfactant; (b) amphoteric surfactant present in said composition at a level of at least about 0.75 parts by weight per part by weight of said anionic surfactant; and (c) from about 0.10 to about 4% by weight of a therapeutic agent selected from the group consisting of 1-imidazolyl-1-(4-chlorophenoxy)-3,3-dimethylbutan-2-one, (climbazole) acetylsalicylic acid, salicylic acid, 2,4,4, '-trichloro-2'-hydroxy diphenyl ether (triclosan); 1-acetyl-4-(4-((2-(2,4-dichlorophenyl)-2-(1H-imidazolyl-1-methyl)-1, 3-dioxolan-4-yl)methoxy)phenyl)-piperazine (Ketoconazole); 1-hydroxy-4-methyl-6-(2,4,4-trimethylpentyl)-2-pyridone monoethonolamine salt (picrotone olamine); selenium sulfide; zinc pyrithione; coal tar; sulfur; 2-(4'-isobutylphenyl) propionic acid (ibuprofen); and mixtures thereof.

The invention also provides for a method of treating scalp disorders such as scalp irritation and/or itching comprising applying to the hair and scalp compositions of the invention as a shampoo and rinsing the shampoo from the hair after shampooing.

Therapeutic testing of individuals living in tropical climates has demonstrated that the detergent compositions of the invention, particularly in the form of shampoos, serve both to prevent the onset of minor scalp disorders in individuals previously free of disorder and to provide therapeutic healing of such disorders in individuals presented with such disorders.

DETAILED DESCRIPTION OF THE INVENTION

Anionic surfactants normally present in mild detergent compositions, especially shampoo formulations are used not only for detersive or cleansing performance, but because they impart a high degree of foaming characteristics to the detergent composition or shampoo, which enhances consumer appeal. However, the anionics are generally much more irritating to the skin than are the amphoteric or non-ionic surfactants. On the other hand, these latter surfactant types are considerably less foaming than the anionics and are thus less appealing when used as a major or sole surfactant component in a detergent composition or a shampoo.

The present invention is grounded on the discovery that use of a specific combination of anionic and amphoteric surfactants provides a mild surfactant base for a therapeutic aqueous, body cleansing composition, particularly in the form of a shampoo, such that the surfactant system does not tend to counteract or negate the therapeutic benefits afforded by the therapeutic agents present in the body cleansing composition or shampoo.

Suitable anionic surfactants which may be used include the water-soluble alkali metal or ammonium salts having alkyl radicals containing from about 8 to about 22 carbon atoms, the term alkyl being sued to include the alkyl portion of higher acyl radicals. Examples of suitable synthetic anionic surfactants are sodium or ammonium alkyl sulphates, especially those obtained by sulphating higher ($C_8$–$C_{18}$) alcohols produced, for example, from tallow or coconut oil; alkyl ($C_9$–$C_{20}$) benzene sulfonates, particularly sodium linear secondary alkyl ($C_{10}$–$C_{15}$) benzene sulfonates; alkyl glyceryl ether sulfates, especially those ethers of the higher alcohols derived from tallow or coconut oil and synthetic alcohols derived from petroleum; coconut oil fatty monoglyceride sulfates and sulfonates; salts of sulfuric acid esters of higher ($C_8$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and potassium salts of fatty acid amides of methyl taurine; alkane monosulfonates such as those derived from reacting alpha-olefins ($C_8$–$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$–$C_{20}$ alpha-olefins, with $SO_3$ and then neutralizing and hydrolyzing the reaction product. The preferred anionic surfactants are sodium or ammonium ($C_{10}$–$C_{18}$) alkyl sulfates and ($C_{10}$–$C_{18}$) alkyl polyethoxy (1–11 Eo) sulfates and mixtures thereof having differing water solubilities.

Particularly preferred anionic surfactant comprises a mixture of a $C_{10}$ to $C_{18}$ alkyl sodium or ammonium sulfate or sulfonate or a $C_{14}$–$C_{18}$ alpha-olefin sodium or ammonium sulfonate (AOS) and a $C_8$ to $C_{12}$ alkyl polyethoxy (2–4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also preferred.

The amount of anionic surfactant present in the composition will generally range from about 4 to 12% by weight (active ingredient), more preferably from about 6 to 10% by weight.

The second essential component of the formulation is an amphoteric surfactant, present at a level of at least about 0.75 parts by weight per 1 part by weight of the content of anionic surfactant present in the composition. The preferred level of amphoteric surfactant is in the range of from about 0.75 to 1.25 parts by weight, more preferably from about 0.9 to 1.1. parts by weight per 1 part by weight of anionic surfactant. It has been found that the presence of one or more amphoteric surfactants at these levels tends to cancel out the tendency of most anionic surfactants to cause irritation when contacted with the skin or scalp.

Examples of amphoteric surfactants which may be used in the compositions of the invention include betaines and compounds which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, N-higher alkyl aspartic acids and the products sold under the trade name "Miranol".

Examples of betaines useful herein include the high alkyl betaines such as coco dimethyl carboxymethyl betaine, lauryl dimethyl carboxymethyl betaine, lauryl dimethyl alpha-carboxymethyl betaine, cetyl dimethyl carboxymethyl betaine, lauryl bis(2-hydroxypropyl) carboxymethyl betaine, oleyl dimethyl gamma-carboxypropyl betaine, lauryl bis-(2-hydroxypropyl) alpha-carboxymethyl betaine and the like.

Other suitable sulfobetaines include 1-(lauryl, dimethylammonio) acetate-1-(myristyl dimethylammonio) propane-3-sulfonate and 1-(myristyl dimethylamino)-2-hydroxypropane-3-sulfonate.

Particularly preferred betaines are those having the following general formula:

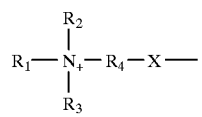

wherein $R_1$ is an alkyl group having from about 10 to 20 carbon atoms, preferably 12 to 16 carbon atoms or the amino radical:

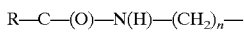

wherein R is an alkyl group having about 10 to 20 carbon atoms and n is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group; and X is an anion selected from the group consisting of $SO_3$= and COO=. Typical alkyl-dimethyl betaines include decyl dimethyl betaine or 2-(N-decyl-N,N-dimethylammonio) acetate, coco dimethyl betaine or 2-(N-coco-N,N-dimethylammonio) acetate, myristyl dimethyl betaine, cetyl dimethyl betaine, stearyl dimethyl betaine, etc. Typical sulfobetaines or sultaines similarly include coco dimethyl sulfobetaine, or 3-(N-coco-N,N-dimethyl ammonio) propane-1 sulfonate, myristyl dimethyl sulfobetaine, or 3-(N-coco-N,N-dimethyl ammonio) propane-1 sulfonate, myristyl dimethyl sulfobetaine, palmityl dimethyl sulfobetaine, lauryl dimethyl sulfobetaine, etc. The amidobetaine and amidosulfobetaines similarly include cocoamidoethyl betaine, cocoamidoethylsulfobetaine, cocoamidopropyl betaine, cocomidopropylsulfobetaine and like materials.

Shampoo formulations containing a combination of anionic and amphoteric surfactants such as betaines present at a level of at least about 0.75 parts by weight betaine per part by weight of anionic surfactant are disclosed in copending U.S. patent application Ser. No. 08/155,251, the complete disclosure of which is incorporated herein by reference.

The composition may also contain one or more non-ionic surfactants which assist in the formation of more stable aqueous compositions, which compositions may be in the form of solutions or dispersions, particularly suspensions or emulsions. The non-ionics, where used, are generally present as a surfactant minor, generally at levels below 10% by weight, more preferably below 5% by weight of the composition.

Suitable nonionic surfactants include, in particular, the reaction products of compounds having a hydrophobic group and a reactive hydrogen atom, for example aliphatic alcohols, acids, amides and alkyl phenols with alkylene oxides, especially ethylene oxide, either alone or with propylene oxide. Specific nonionic surfactant compounds are alkyl ($C_6$–$C_{18}$) primary or secondary linear or branched alcohols condensed with ethylene oxide, and products made by condensation of ethylene oxide with the reaction products of propylene oxide and ethylenediamine. Other so-called nonionic surfactant compounds include long chain tertiary amine oxides, long-chain tertiary phosphine oxides, dialkyl sulfoxides, fatty ($C_8$–$C_{18}$) esters of glycerol. sorbitan and the like, alkyl polyglycosides, ethoxylated glycerol esters, ethyoxylated sorbitans and ethoxylated phosphate esters.

A more detailed illustration of the various surfactants and classes of surfactants mentioned may be found in the text *Surface Active Agents*, Vol. II, by Schwartz, Perry and Berch (Interscience Publishers, 1958), in a series of annual publications entitled McCutcheon's Detergents and Emulsifiers, issued in 1969, or in *Tenside-Taschenbuch*, H. Stache, 2nd Ed. Carl Hanser Verlag, Munich and Vienaa, 1981.

The therapeutic agent present in the composition is selected from the group consisting of climbazole, acetylsalicylic acid, salicylic acid, triclosan, ketoconazole, piroctone olamine, selenium sulfide, zinc pyrithione, coal tar, sulfur, ibuprofen and mixtures thereof, present at a level of from about 0.10 to about 4% by weight.

The therapeutic agent preferably present in the composition of the invention is climbazole which is known chemically as 1-imidazolyl-1-(4-chlorophenoxy)-3,3- dimethylbutane-2-one or equivalent imidazolyl compounds. This agent may be prepared by reacting 1-bromo-1-(4-chlorophenoxy)-3-dimethylbutan-2-one with imidazole dissolved in acetonitrile as disclosed in U.S. Pat. Nos. 3,812,142 and 3,903,287. This imidazolyl ketone is a water insoluble crystalline powder having a melting point of 94.5°–97.8° C., and may be obtained from the Bayer Company.

Climbazole has proven a more effective therapeutic in compositions having a pH on the acid side, e.g. from about 4.0 to about 6.9, more preferably from about 4.5 to 6.5. Adjustment of the pH of the shampoo formulation with a suitable acid, e.g. citric acid, may be necessary. Suitable acid buffers such as boric acid and phosphoric acid may also be used.

A combination of climbazole with one or more keratolytic or anti-inflammatory agents such as acetylsalicylic acid (aspirin), salicylic acid, 2,4,4'-trichloro-2'-hydroxy diphenyl ether (triclosan); 2-(4'-isobutylphenyl) propionic acid (ibuprofen); 1-acetyl-4-(4-((2-(2,4-dichlorophenyl)-2-(1H-imidazolyl-1-methyl)-1,3-dioxolan-4-yl)methoxy)phenyl)-piperazine (Ketoconazole); 1-hydroxy-4-methyl-6-(2,4,4-trimethylpentyl)-2-pyridone monoethonolamine salt (piroctone olamine); coal tar; selenium sulfide; sulfur or zinc pyrithione is also within the scope of the invention. Addition of one or more of these therapeutics serves the dual roles of pH adjustment (where the additive is acid) as described above, and as a co-therapeutic along with the climbazole. Use of the combination can also impart improved hair conditioning effects to the shampoo as will be hereinafter described. The climbazole is normally present in the shampoo at a level effective to provide therapeutic relief of the scalp disorders described herein. Preferred levels are in the range of about 0.1 to about 4% by weight, more preferably from about 0.25 to 2.5% by weight and most preferably from about 0.5 to 1.5% by weight. When used with a co-therapeutic, e.g. salicylic acid, the co-therapeutic may be present at a level of from about 0.1 to about 10% by weight, more preferably from about 0.25 to about 4% by weight and most preferably from about 0.25 to 2.5% by weight.

The body cleansing composition of the present invention may also be formulated as a hair conditioning shampoo and therefore may contain one or more hair conditioning agents and suspending agents.

Suitable hair conditioning agents include organosilicon compounds, e.g., non-volatile silicones and aminosilicones such as dimethicone. The conditioner may also comprise water insoluble polyethylenes; paraffins; petrolatums; microcrystalline waxes; $C_{18}$–$C_{36}$ mixed fatty acids and corresponding triglycerides; stearyl stearate and like known conditioners.

Conditioners may also include various cationic quaternary ammonium salts or polymers. Preferred quaternary ammonium salts include materials such as tricetyl methyl ammonium chloride, dicetyl dimethyl ammonium chloride, distearyl dimethyl ammonium chloride, tristearyl methyl ammonium chloride and other quaternaries such as: guar hydroxypropyl trimethylammonium chloride (Cosmedia GUAR-C261, available from Hoechst Celanese Corp.); polyethylene glycol (PEG 15) coco-polyamine (Polyquat® H81, available from Henkel G.m.b.H.); quaternized hydroxyethyl cellulose, available from Amerchol as Polymers JR and LR; polymers of dimethyldiallyl ammonium chloride or copolymers thereof with acrylamide, available as Merquats 100 and 550 (also known as polyquaternium 10 and 7 respectively); vinyl imidazole vinyl pyrrolidone copolymers, available as Luviquats from BASF Corp.; poly-vinyl pyrrxolidone-dimethylaminoethyl methacrylate copolymers, available as GAFQUATS from GAF Corp.; and like materials. The quaternary conditioners are normally present in the composition at levels of from about 0.2 to about 5% by weight.

Hair conditioning shampoos also contain one or more suspending agents or lipids which assist in maintaining a stable dispersion of non-water soluble ingredients and also impart improved hair conditioning effects, generally present at a level of from about 1 to 15% by weight. Suitable of such agents include long chain acyl derivatives such as $C_{16}$ to $C_{50}$ fatty acid esters of polyols such as glycerol, ethylene glycol or sorbitol. Preferred agents of this class include glycerol distearate and isosteareth (2 or 10), as well as long chain alkanolamides such as stearamide DEA distearate. Suspending agents of this type are normally present in the composition at a level of from about 0.5 to about 5% by weight of the composition.

Other useful suspension stabilizers are long chain primary alcohols or ethoxylated alcohols averaging about 26 to 40 carbon atoms in the chain. These alcohols are mixed alcohols wherein at least about 80% of the chain lengths are of 18–44 carbon atoms for alcohols averaging 30 carbon atoms and at least 80% of the chain lengths are 30–54 carbon atoms for alcohols averaging 40 carbon atoms. These materials are available from Petrolite Corporation under the trade name UNILIN™ alcohols. Preferred materials are Unilin™ 425 alcohol (30 carbon chain average), Unilin™ 550 alcohol (40 carbon chain average) and Unilin™ 350 (26 carbon chain average). A suitable derivative is Unithox™-550 which is an ethoxylated (13 EO) alcohol averaging 40 carbon atoms in the alkyl chain. These alcohols are normally present in the composition at levels of from about 1 to about 7% by weight.

The shampoo composition also contains water, preferably deionized or irradiated water. The amount of water present in the composition as added water plus water present in the ingredients used in the formula will generally range from about 50 to about 85% by weight, more preferably from about 60 to about 80% by weight.

In addition to the previously mentioned constituents of the liquid shampoo, normal and conventional adjuvants may be present, provided they do not adversely affect the properties of the shampoo. Thus, there may be used various coloring agents and perfumes, ultraviolet light absorbers such as the Uvinuls, which are products of GAF Corporation, preservatives such as formaldehyde or hydrogen peroxide; pearlescing agents and opacifiers, solvents, such as ethanol, glycerin and glycols (ethylene glycol is useful as a clarifying agent, to prevent high and low temperature clouding of desirably clear shampoos); lubricants, such as mineral oil and higher fatty alcohols, e.g. cetyl alcohol, stearyl alcohol; sequestering agents such as EDTA tetrasodium salt, thickening agents such as hydroxypropyl methyl cellulose (Methocel 34M) and salts such as sodium chloride, etc. The proportion of such adjuvant material, in total, will normally not exceed 5% of the shampoo.

The shampoos are readily made by simple mixing methods from readily available components which, on storage, do not adversely affect the entire composition. However, it is preferred that the imidazolyl compound be first mixed with a nonionic component prior to the addition of the amphoteric and anionic surfactants. However, in the absence of a nonionic surfactant, the Climbazole can also be mixed with an aqueous solution of the amphoteric betaine prior to the addition of the anionic surfactant. Thus, the products are capable of being made in desired clear form or in opaque or opalescent form. The viscosities are adjustable by changing the total percentage of active ingredients and by modifying the percentages of thickening agent, sodium chloride and other adjuvants. The viscosity of the shampoo will normally be about that of glycerin at room temperature, e.g., about 1,000 centipoises, but the viscosity may be in the broader ranges of 250–1500 centipoises. Its viscosity may approximate those of commercially acceptable shampoos now on the market. Instead of measuring viscosity directly, as by a Brookfield LVF viscometer, one may employ standard laboratory flow tests, in which flow times through a restriction or tube length under a reproducible head are measured in seconds, utilizing a Raymond tube. Viscosities may preferably range from 10–135 seconds and up to 300 or 400 seconds. The shampoo itself remains stable on storage for lengthy periods of time, without color changes or settling out of any insoluble materials.

The following examples are illustrative of the invention.

EXAMPLE 1

A shampoo composition was prepared by the general mixing procedure described above. The formulation of this shampoo is as follows in weight %:

| COMPONENT | AS IS | % |
|---|---|---|
| ACTIVES | | |
| Cocoamido Propyl Betaine No. 3 | 30.0 | 9.0 |
| Deionized water (irradiated) | 25.0 | — |
| Sodium Deceth Sulfate (3 Eo) | 15.0 | 4.5 |
| Ammonium Lauryl Sulfate | 12.0 | 3.0 |
| Sodium Cumene Sulfonate | 5.0 | 2.3 |
| $C_{30}$–$C_{40}$ Fatty Alcohol (UNILIN ™) | 4.0 | 4.0 |
| Dimethyl Polysiloxane | 3.5 | 3.5 |
| Distearyl Methyl Ammonium Chloride | 1.0 | 1.0 |
| Preservative | 1.0 | 1.0 |
| Isosteareth (2 Eo) | 0.8 | 0.8 |
| Perfume | 0.75 | 0.75 |
| Hydroxy Ethyl Cellulose | 0.6 | 0.6 |
| Climbazole | 0.5 | 0.5 |
| Polyquaternium 10 | 0.35 | 0.35 |
| Sodium Phosphate (Di Basic) | 0.2 | 0.2 |
| EDTA | 0.1 | 0.06 |
| Colorant | 0.013 | 0.013 |

This shampoo was designated as Formula A.

EXAMPLE 2

A second shampoo was prepared having the formula of Example 1 except that the amount of climbazole was raised to 1.5% by weight and 1.5% by weight less water was added to the formulation. This formulation was designated as Formula B.

The effectiveness of the shampoo formulations of the present invention for healing and preventing scalp disorders was evaluated using the following protocol. Ninety residents of the Dominican Republic who were free of scalp disease (as determined by a dermatologist), but who regularly complained of scalp irritation and itching occasioned by shampoo usage were selected by questionnaire. The group was arbitrarily divided into six groups of 15 each.

Four groups were used to evaluate the effectiveness of Formulas A and B above in reducing scalp discomfort (itchiness) for those complaining of discomfort after shampooing with a control formulation containing a high content of anionic surfactant. The control formulation used was a formulation containing no therapeutic agent and a surfactant mixture high in anionic content. The surfactant combination (actives) in the control were:

| | | |
|---|---|---|
| Ammonium lauryl sulfate | 19 | wt. % |
| Cocamide DEA* | 4.5 | wt. % |
| Sodium cumene sulfonate | 1.4 | wt. % |
| Na laureth –13 carboxylate | 2.5 | wt. % |

*CTFA adopted name for Coconut Diethanolamide

Each of the four panels were shampooed with the control product every other day for two weeks for a total of seven washes. The shampoo procedure involved the application of 10 grams of the control directly to the wet scalp followed by a one minute massage into the scalp. The hair is then washed and rinsed free of lather and dried.

Scalp evaluations were made by the subjects themselves and a dermatologist after 6, 10 and 14 days to determine the degree of scalp discomfort occasioned by shampooing using the control. Ratings of itching, irritation (redness of skin), dryness and flaking were made on a scale of 1 to 10, with 1 representing no problem and 10 representing maximum problem.

The average score for each of the four groups at the end of the control washing for each of the four scalp discomfort factors was plotted as a base line value.

The four control groups were then subjected to seven additional shampooings using the protocol described above over the next two weeks using the following shampoos:

Group A—Formula A.
Group B—Formula B.
Group C—Commercial HEAD AND SHOULDERS™ product obtained in Mexico (H&S)*
* Major surfactant is anionic.
Group D—Commercial PANTENE™ Scalp Care/Anti Dandruff product obtained in the Philippines.*
* Major surfactant is anionic.

Scalp evaluations for each group were made after the 3rd, 5th and 7th washes, rated on a 1–10 scale as described above and plotted as a fitted regression line for each group vs. the baseline values obtained after the control washings.

Scalp changes are shown in Table 1. The more negative the change, the better the improvement of the scalp condition.

TABLE 1

| SHAMPOO | ITCH-ING | IRRI-TATION | DRY-NESS | FLAKING | CONCLU-SION |
|---|---|---|---|---|---|
| PANTENE | −0.28 | −0.35 | −0.28 | −1.75 | marginally effective |
| H&S | 0.18 | −0.28 | 1.05 | −2.05 | marginally effective |
| Form B | −2.10 | −0.15 | −3.93 | −5.30 | most effective |
| Form A | −1.25 | −1.00 | −1.00 | −3.72 | effective |

These results show that the products of the present invention are considerably more effective than leading commercial anti-dandruff shampoos (which contain anionic surfactant as the major surfactant component) in reducing or substantially eliminating scalp disorder factors occasioned by the use of an irritating, high anionic content shampoo.

The remaining two groups of 15 panelists each (Group E and F) were subjected to a different protocol. In this protocol, there were no control washings, but instead the hair of each panelist was washed every other day by the washing procedure described above (for a total of 14 washings) with HEAD AND SHOULDERS™ (Group E) and with Formula B (Group F). The objective of this protocol was to determine the effectiveness of each product to prevent the onset of scalp disorders. As above, a baseline evaluation of scalp disorder for each panelist prior to the 14 washings was established by dermatological observation and panelist input.

Changes in scalp characteristics after 14 washes rated on a 1–10 scale were plotted as above. Results are shown in

TABLE 2

| SHAMPOO | ITCH-ING | IRRI-TATION | DRY-NESS | FLAKING | CONCLU-SION |
|---|---|---|---|---|---|
| H and S | −2.42 | −0.07 | 0.08 | −2.98 | marginally effective |
| Form B | −2.69 | −1.49 | −4.93 | −4.84 | effective |

The results show that the product of the invention is considerably more effective in preventing the onset of scalp disorder problems than a leading commercial brand. Again, it is believed that the major factor contributing to this efficacy is the mild surfactant system present in the formulations of this invention.

An additional feature of the invention is based on the discovery that mild conditioning shampoos of the invention which contain an alkyl, alkaryl or alpha olefin sulfonate as the main anionic surfactant and a combination of climbazole and salicylic acid or acetylsalicylic acid also provide improved conditioning effects in an acid shampoo (pH 4.0–5.0). Two shampoo formulations containing the following surfactant and therapeutic ingredient compositions were prepared:

|  | Example 3 | Example 4 |
|---|---|---|
| Climbazole | 1.5 | — |
| Salicylic Acid | 2.0 | — |
| Sodium AOS (40%) | 22.5 | 22.5 |
| Na Cumene Sulfonate (43.3%) | 7.0 | 7.0 |
| Cocoamidopropyl Betaine (30%) | 30.0 | 30.0 |

The remainder of each formulation was identical and essentially as described Examples 1 and 2. The pH of each formula was adjusted to 4.0 using citric acid.

Hair washed with the shampoo of Example 3 exhibited improved compatibility as compared with hair washed using the Example 4 formulation. This is indicative of an increased deposition on the hair of the cationic hair conditioning components present in the formula of Example 3 as a result of the presence of the therapeutic agents climbazole and salicylic acid.

What is claimed is:

1. A mild, aqueous unbuilt, skin care, detergent composition consisting essentially of:

(a) from about 6 to 10% by weight of an anionic surfactant selected from the group consisting of water soluble salts of C8–C18 alkyl sulfates, C9–C20 alkyl benzene sulfonates, C8–C18 alkyl glyceryl ether sulfates, C8–C18 alkyl polyethoxy sulfates, C8–C18 acyl isethionates, C8–C18 acyl taurates, C8–C20 alkane sulfonates, C10–C20 olefin sulfonates and mixture thereof;

(b) an amphoteric surfactant selected from the group consisting of betaines having the formula

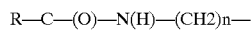

wherein $R_1$ is an alkyl group having from about 10 to 20 carbon atoms or the amino radical:

$R-C-(O)-N(H)-(CH_2)_n-$ wherein $R_1$ is an alkyl group having about 10 to 20 carbon atoms and n is the integer 1–4; $R_2$ and $R_3$ are each alkyl groups having 1 to 3 carbons; $R_4$ is an alkylene or hydroxyalkylene group having from 1 to 4 carbon atoms; and X is an anion selected from the group consisting of $SO_3=$ and $COO=$; and a derivative of a secondary or tertiary amine containing a C8–C18 aliphatic group and a solubilizing group selected from the group consisting of carboxy, sulfonate, sulfate, phosphate and phosphonate in its molecular structure at a level of about 0.75 to 1.25 parts by weight per part by weight of said anionic surfactant;

(c) an effective amount of 1-imidazolyl-1-(4-chlorophenoxy)-3,3-dimethylbutan-2-one (climbazole); and mixtures thereof; and (d) about 50 to 85% by weight of water; said composition being effective to provide therapeutic effects on skin disorders such as itching, irritation and dryness.

2. The composition of claim 10 wherein said amphoteric surfactant is said betaine, said anionic surfactant is a mixture of a surfactant selected from the group consisting of the sodium or ammonium C10 to C18 alkyl sulfates, C10 to C18 alkyl sulfonates and C14 to C18 alpha olefin sulfonates with a sodium or ammonium C8 to C12 alkyl polyethoxy sulfate and said composition has a pH of about 4 to about 6.9.

3. The composition of claim 14 wherein said hair conditioning agent comprises a quaternary ammonium salt selected from the group consisting of tricetyl methyl ammonium chloride, dicetyl dimethyl ammonium chloride, distearyl dimethyl ammonium chloride, tristearyl methyl ammonium chloride and mixtures thereof.

4. The composition of claim 8 wherein said amphoteric surfactant is said betaine, said anionic surfactant includes an alkyl, alkaryl or an alpha olefin sulfonate as the main anionic surfactant and 0.2 to 5% by weight of a water-insoluble hair conditioning agent is present in addition, said conditioning shampoo composition having a pH of 4 to 5 and exhibiting better conditioning than the same composition without a therapeutic agent.

5. The composition of claim 14 wherein said amphoteric surfactant is said betaine, said anionic surfactant is a mixture of a surfactant selected from the group consisting of the sodium or ammonium C10 to C18 alkyl sulfates, C10 to C18 alkyl sulfonates and C14 to C18 alpha olefin sulfonates and a C8 to C12 polyethoxy sulfate, said composition includes 0.2 to 5% by weight of said water-insoluble hair conditioning agent and said composition has a pH of about 4 to 6.9.

6. The composition of claim 4 which further contains 0.5–7% by weight of a long chain alcohol or ethoxylated alcohol averaging about 26 to 40 carbon atoms as a suspending agent.

7. The composition of claim 5 which further contains 0.5–7% by weight of a long chain alcohol or ethoxylated alcohol averaging about 26 to 40 carbon atoms as a suspending agent.

8. The composition of claim 1 containing from about 0.9 to 1.1 parts by weight of said amphoteric surfactant per part by weight of anionic surfactant.

9. The composition of claim 1 wherein said detergent composition is a shampoo.

10. The composition of claim 9 wherein 1-imidazolyl-1-(4-chlorophenoxy)-3,3-dimethylbutan-2-one is present at a level of from about 0.1 to 4% by weight.

11. The composition of claim 10 wherein said 1-imidazolyl-1-(4-chlorophenoxy)-3,3-dimethylbutan-2-one is present at a level of from about 0.25 to about 2.5% by weight.

12. The composition of claim 9 wherein said amphoteric surfactant is a betaine or sulfobetaine.

13. The composition of claim 9 wherein said betaine is alkylamidoethyl betaine or alkylamidoethyl betaine.

14. The composition of claim 2 further containing a hair conditioning agent selected from the group consisting of organosilicone compounds, aminosilicones, water insoluble hydrocarbons, water insoluble fatty acid esters, quaternary ammonium salts and mixtures thereof, present at a level of from about 0.2 to 5% by weight.

15. The composition of claim 14 wherein said conditioner is a polysiloxane or aminopolysiloxane.

16. The composition of claim 14 wherein said quaternary ammonium salt is the salt of a polymer of dimethyl ammonium chloride or copolymers thereof with acrylamide.

17. The composition of claim 14 further containing one or a mixture of suspending agents present at a level of from about 0.5 to 7% by weight.

18. The composition of claim 17 wherein said suspending agent is a long chain alcohol or ethoxylated alcohol averaging about 26 to 40 carbon atoms.

* * * * *